US010441387B2

(12) United States Patent
Jorneus et al.

(10) Patent No.: US 10,441,387 B2
(45) Date of Patent: Oct. 15, 2019

(54) ABUTMENT SYSTEM AND DENTAL METHODS

(71) Applicant: Nobel Biocare Services AG, Zurich-Flughafen (CH)

(72) Inventors: Lars Jorneus, Frillesas (SE); Eric Rompen, Liege (BE); Eric Van Dooren, Antwerp (BE); Bernard Touati, Paris (FR)

(73) Assignee: NOBEL BIOCARE SERVICES AG, Kloten (CH)

(*) Notice: Subject to any disclaimer, the term of this patent is extended or adjusted under 35 U.S.C. 154(b) by 0 days.

(21) Appl. No.: 13/931,118

(22) Filed: Jun. 28, 2013

(65) Prior Publication Data

US 2014/0011160 A1    Jan. 9, 2014

(30) Foreign Application Priority Data

Jul. 9, 2012   (GB) .................................. 1212125.7

(51) Int. Cl.
*A61C 8/00* (2006.01)

(52) U.S. Cl.
CPC ............ *A61C 8/008* (2013.01); *A61C 8/0066* (2013.01); *A61C 8/0068* (2013.01); *A61C 8/0078* (2013.01); *A61C 8/006* (2013.01); *A61C 8/0069* (2013.01); *F04C 2270/0421* (2013.01)

(58) Field of Classification Search
CPC ....... A61C 8/005; A61C 8/006; A61C 8/0066; A61C 8/008; A61C 8/0068; A61C 8/0078; A61C 8/0069; F04C 2270/0421
USPC ...................................... 433/173–176, 201.1
See application file for complete search history.

(56) References Cited

U.S. PATENT DOCUMENTS

| 4,178,686 | A | | 12/1979 | Riess et al. |
| 4,713,004 | A | * | 12/1987 | Linkow et al. ............... 433/174 |
| 5,015,186 | A | | 5/1991 | Detsch |
| 5,035,619 | A | | 7/1991 | Daftary |
| 5,040,982 | A | * | 8/1991 | Stefan-Dogar ........ A61C 8/005 433/169 |
| 5,040,983 | A | | 8/1991 | Binon |

(Continued)

FOREIGN PATENT DOCUMENTS

| EP | 0 801 544 | 10/1997 |
| EP | 0 868 889 | 10/1998 |

(Continued)

OTHER PUBLICATIONS

Marlin et al., "Restoring the Single Lower Incisor Implant with Esthetics, Antirotation, and Retrievability". Compendium: The Compendium of Continuing Education in Dentistry. vol. XV, No. 5, May 1994 pp. 624-630.

*Primary Examiner* — Cris L. Rodriguez
*Assistant Examiner* — Hao D Mai
(74) *Attorney, Agent, or Firm* — Knobbe, Martens, Olson & Bear, LLP

(57) ABSTRACT

The present application relates to an abutment system (12) and its use. The abutment system (12) comprises: a soft tissue level abutment part (10) adapted to be attached to a bone level dental implant (40) by means of an abutment screw (56), wherein the abutment system is adapted to selectively support both a cement-retained final restoration (66) and a screw-retained prosthetic component (68; 70). The present application also relates to dental methods.

18 Claims, 9 Drawing Sheets

(56) References Cited

U.S. PATENT DOCUMENTS

| | | | |
|---|---|---|---|
| 5,049,073 A * | 9/1991 | Lauks | A61C 8/0018 433/169 |
| 5,071,351 A * | 12/1991 | Green, Jr. | A61C 8/0012 433/173 |
| 5,135,395 A | 8/1992 | Marlin | |
| 5,169,309 A | 12/1992 | Staubli et al. | |
| 5,238,405 A | 8/1993 | Marlin | |
| 5,281,140 A | 1/1994 | Niznick | |
| 5,350,302 A | 9/1994 | Marlin | |
| 5,362,235 A * | 11/1994 | Daftary | A61C 8/0048 433/172 |
| 5,439,380 A | 8/1995 | Marlin | |
| 5,527,182 A * | 6/1996 | Willoughby | 433/172 |
| 5,662,476 A | 9/1997 | Ingber et al. | |
| 5,674,069 A | 10/1997 | Osorio | |
| 5,759,036 A | 6/1998 | Hinds | |
| 5,810,592 A | 9/1998 | Daftary | |
| 5,829,977 A | 11/1998 | Rogers et al. | |
| 5,873,721 A * | 2/1999 | Willoughby | 433/173 |
| 5,873,722 A | 2/1999 | Lazzara et al. | |
| 5,882,200 A * | 3/1999 | Sutter | A61C 8/0001 433/173 |
| 5,890,902 A * | 4/1999 | Sapian | A61C 8/0048 433/173 |
| 5,904,483 A * | 5/1999 | Wade | A61C 8/0048 433/173 |
| 5,947,733 A | 9/1999 | Sutter et al. | |
| 6,068,478 A | 5/2000 | Grande et al. | |
| 6,126,445 A * | 10/2000 | Willoughby | 433/223 |
| 6,155,828 A | 12/2000 | Lazzara et al. | |
| 6,164,969 A * | 12/2000 | Dinkelacker | A61C 8/0018 433/173 |
| 6,168,435 B1 * | 1/2001 | Beaty | A61C 8/005 433/172 |
| 6,227,856 B1 | 5/2001 | Beatu et al. | |
| 6,358,050 B1 | 3/2002 | Bergstrom et al. | |
| 6,386,876 B1 | 5/2002 | Lee | |
| 6,540,514 B1 | 4/2003 | Falk | |
| 6,558,162 B1 | 5/2003 | Porter et al. | |
| 6,769,913 B2 | 8/2004 | Hurson | |
| 6,790,040 B2 | 9/2004 | Amber et al. | |
| 6,969,256 B2 | 11/2005 | Sethi et al. | |
| 7,632,095 B2 * | 12/2009 | Ostman | A61C 5/08 433/172 |
| 7,632,096 B2 | 12/2009 | Gittleman | |
| 7,922,488 B2 | 4/2011 | Falk et al. | |
| 8,033,826 B2 | 10/2011 | Towse et al. | |
| 8,057,229 B2 * | 11/2011 | Engstrom | A61C 8/005 433/173 |
| 8,419,429 B2 | 4/2013 | Wang | |
| 8,612,037 B2 | 12/2013 | Powell et al. | |
| 8,794,966 B2 | 8/2014 | Hung | |
| 2002/0127518 A1 | 9/2002 | Lustig et al. | |
| 2003/0148246 A1 | 8/2003 | Lustig et al. | |
| 2004/0063069 A1 * | 4/2004 | Lombardi | A61C 8/005 433/173 |
| 2005/0181331 A1 | 8/2005 | Lustig et al. | |
| 2007/0037122 A1 * | 2/2007 | Bassett | A61C 8/0001 433/173 |
| 2007/0037123 A1 * | 2/2007 | Mansueto | A61C 8/0022 433/173 |
| 2007/0059666 A1 | 3/2007 | Zickman et al. | |
| 2007/0072149 A1 | 3/2007 | Rompen et al. | |
| 2007/0072150 A1 * | 3/2007 | Mansueto | A61C 8/0022 433/174 |
| 2007/0099152 A1 | 5/2007 | Busch | |
| 2008/0233539 A1 | 9/2008 | Rossler et al. | |
| 2008/0241792 A1 * | 10/2008 | Rossler | A61C 8/0022 433/174 |
| 2009/0130629 A1 | 5/2009 | Towse et al. | |
| 2009/0220916 A1 | 9/2009 | Fisker et al. | |
| 2009/0298015 A1 | 12/2009 | Al-Attar | |
| 2009/0305190 A1 | 12/2009 | Zipprich | |
| 2010/0167239 A1 | 7/2010 | Guillard | |
| 2010/0303316 A1 | 12/2010 | Bullis et al. | |
| 2010/0311011 A1 | 12/2010 | Schwieder et al. | |
| 2011/0097688 A1 | 4/2011 | Alberto | |
| 2011/0117522 A1 | 5/2011 | Verma et al. | |
| 2011/0189634 A1 | 8/2011 | Kfir | |
| 2011/0200968 A1 | 8/2011 | Laizure | |
| 2011/0262884 A1 | 10/2011 | Zena et al. | |
| 2012/0237899 A1 * | 9/2012 | Holmstrom | A61C 8/0001 433/174 |
| 2012/0251979 A1 | 10/2012 | Karim et al. | |
| 2012/0295226 A1 | 11/2012 | Robb et al. | |
| 2012/0301850 A1 * | 11/2012 | Sollberger | A61C 8/005 433/174 |
| 2013/0196290 A1 | 8/2013 | Herrington et al. | |
| 2014/0011155 A1 | 1/2014 | Thomsen | |
| 2014/0178835 A1 | 6/2014 | Lin | |
| 2014/0205969 A1 | 7/2014 | Marlin | |
| 2015/0037757 A1 * | 2/2015 | Kwan | A61C 8/0051 433/174 |
| 2017/0056132 A1 * | 3/2017 | Kwan | A61C 8/008 |

FOREIGN PATENT DOCUMENTS

| | | |
|---|---|---|
| EP | 2 088 957 | 5/2008 |
| EP | 2 010 092 | 1/2009 |
| EP | 2 242 442 | 10/2010 |
| EP | 2 313 021 | 4/2011 |
| FR | 2317904 A | 2/1977 |
| JP | 2001-510705 | 8/2001 |
| JP | 2010-524606 | 7/2010 |
| WO | WO 99/04723 | 2/1999 |
| WO | WO 2007/121939 | 11/2007 |
| WO | WO 2008/128756 A2 | 10/2008 |
| WO | WO 2009/149881 | 12/2009 |
| WO | WO 2010/056330 | 5/2010 |

* cited by examiner

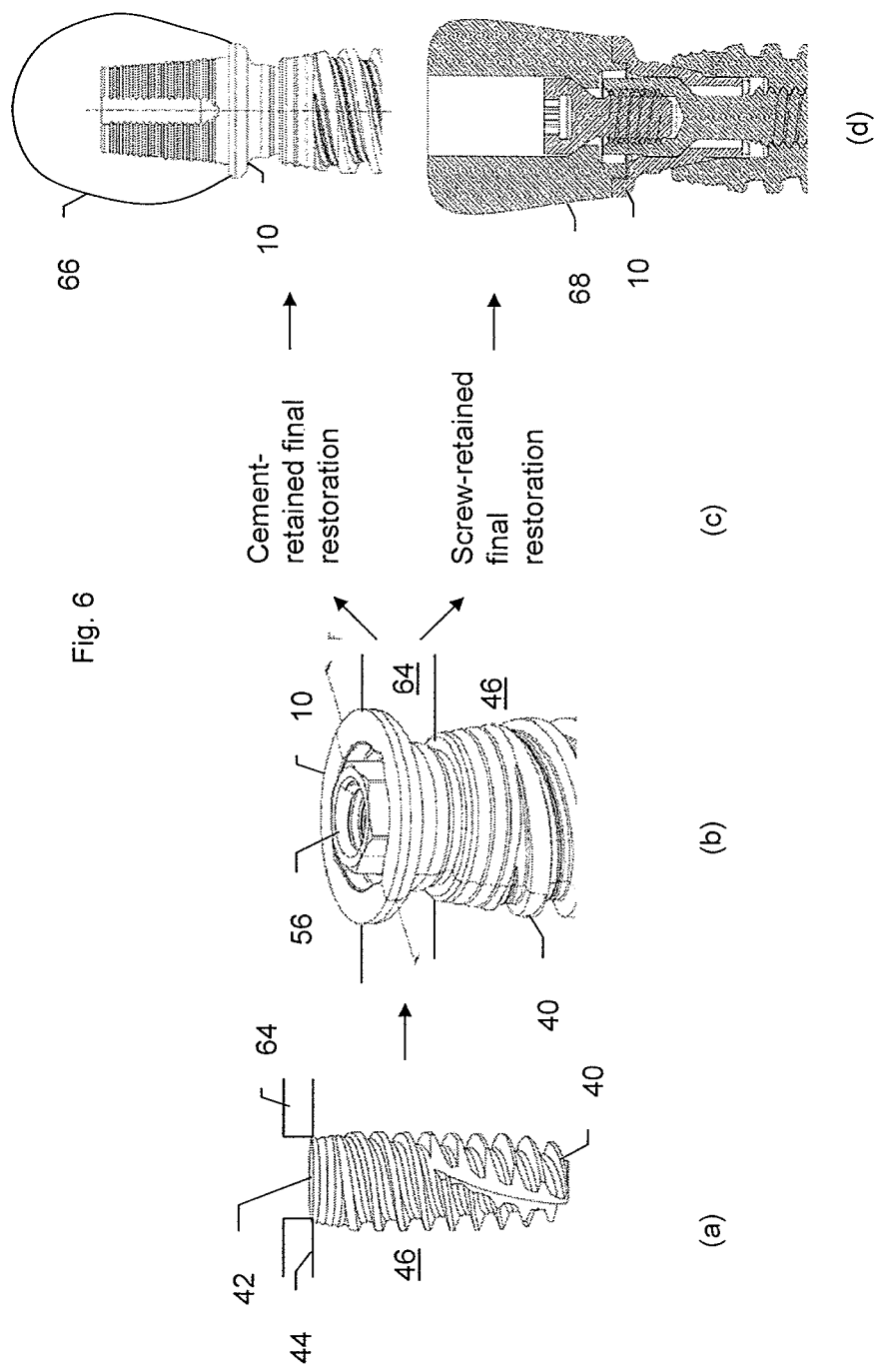

ABUTMENT SYSTEM AND DENTAL METHODS

CROSS-REFERENCE TO RELATED APPLICATIONS

This application claims the priority benefit of British Patent Application No. GB1212125.7, filed on Jul. 9, 2012, the entire contents of which is herein incorporated by reference in its entirety.

BACKGROUND

Field of Invention

The present invention relates to an abutment system and its use. The present invention also relates to dental methods.

Description of the Related Art

U.S. Pat. No. 5,810,592 (Daftary) discloses a dental implant system made from four pieces: a rounded equilateral triangle shaped healing abutment, a large bolt member, a matching abutment head, and a small bolt member. The healing abutment has an intermediate shoulder for accommodating the gingival tissues which surround the patient's jawbone. Further, the matching abutment head is secured on the healing abutment for supporting a tooth analogue. The large bolt member is used for fastening the healing abutment to an implant fixture. The small bolt member is for securing the abutment head to the healing abutment. However, the dental implant system in U.S. Pat. No. 5,810,592 appears only to support a cement-retained tooth analogue.

U.S. Pat. No. 5,040,983 (Binon) discloses a coping fixed on a dental implant fixture installed in a jawbone. A transmucosal component, penetrating the overlying gum tissue, is fixed to the implant fixture with a screw, the head portion of which has an internally-threaded socket which receives a bolt cooperating with a shoulder to fix the coping on the transmucosal component. The coping is intended for use in removably fixing a temporary dental restoration on the support consisting of the dental implant fixture and its transmucosal component, where a permanent prosthodontic restoration will eventually be fixed. The temporary dental restoration is mounted on and around the coping. However, the system in U.S. Pat. No. 5,040,983 supports only a screw-retained prosthodontic restoration.

SUMMARY

The present invention is defined in the appended independent claims. Embodiments are defined in the appended dependent claims.

According to a first aspect, there is provided an abutment system, comprising: a soft tissue level abutment part adapted to be attached to a bone level dental implant by means of an abutment screw, wherein the abutment system is adapted to selectively support both a cement-retained final restoration and a screw-retained prosthetic component. That is, either a cement-retained final restoration or a screw-retained prosthetic component can be supported using the same soft tissue level abutment part. This makes the abutment system flexible to use.

The abutment system may further comprise a coronal abutment part adapted to be attached to the soft tissue level abutment part by means of a further screw, wherein the coronal abutment part further is adapted to support the cement-retained final restoration.

The prosthetic component may be a screw-retained final restoration adapted to be directly attached to the soft tissue level abutment part by means of a further screw.

The abutment screw may have a coronal internally threaded portion, wherein the further screw has an apical externally threaded portion for engagement with the coronal internally threaded portion of the abutment screw.

The soft tissue level abutment part may have a flat circumferential top surface at the outer perimeter of the coronal end of the soft tissue level abutment part.

The soft tissue level abutment part may have at least one indexing element exposed to the coronal end of the soft tissue level abutment part for preventing rotation of a component attached to the soft tissue level abutment part.

The flat circumferential top surface may have an inner circular perimeter, wherein the at least one indexing element is at least one lobe extending apically from the inner circular perimeter.

The soft tissue level abutment part may have an outer surface devised for exposure to soft tissue. The outer surface may be curved in the coronal-apical direction of the soft tissue level abutment part. The curved outer surface may extend from a larger coronal diameter to a smaller apical diameter first in a convex shape and then in a concave shape.

The soft tissue level abutment part may have an external surface adapted to abut against an internal connection surface of the bone level dental implant.

The abutment system may comprise several soft tissue level abutment parts (of the general type described above) with different diameters and/or heights.

Another aspect relates to the use of an abutment system as described above to selectively support both a cement-retained final restoration and a screw-retained prosthetic component. This aspect may exhibit the same or similar features and advantages as the previously described aspect, and vice versa.

According to yet another aspect, there is provided a dental method, which comprises: providing an abutment system including a universal soft tissue level abutment part adapted to be attached to a bone level dental implant; and attaching the universal soft tissue level abutment part to the bone level dental implant installed in the jawbone of a patient, wherein the abutment system is adapted to selectively support both a cement-retained final restoration and a screw-retained final restoration. This aspect may exhibit the same or similar features and advantages as the previously described aspects, and vice versa.

The universal soft tissue level abutment part may remain attached to the bone level dental implant during subsequent steps of the method, which include: selecting one of a cement-retained final restoration and a screw-retained final restoration; and attaching the selected final restoration to the abutment system.

The universal soft tissue level abutment part may be attached to the bone level dental implant immediately after the bone level dental implant is installed in the jawbone of the patient.

The bone level dental implant may be allowed to at least partly osseointegrate before the selected final restoration is attached.

The bone level dental implant may be installed in the jawbone such that the coronal end of the bone level dental implant is substantially in level with the edge of the jawbone.

The attached universal soft tissue level abutment part may have an outer surface exposed to soft tissue.

According to still another aspect, there is provided a dental method, wherein a universal soft tissue level abutment part of an abutment system is attached to a bone level dental implant installed in the jawbone of a patient, and wherein the abutment system is adapted to selectively support both a cement-retained final restoration and a screw-retained final restoration, which method comprises: selecting one of a cement-retained final restoration and a screw-retained final restoration; and attaching the selected final restoration to the abutment system. This aspect may exhibit the same or similar features and advantages as the previously described aspects, and vice versa.

BRIEF DESCRIPTION OF THE DRAWINGS

These and other aspects of the present invention will now be described in more detail, with reference to the appended drawings showing currently preferred embodiments of the invention.

FIG. 1b is a perspective view of the soft tissue level abutment part of FIG. 1a.

FIG. 2b is a perspective view of the arrangement in FIG. 2a.

FIG. 4a is a side view of the soft tissue level abutment part and dental implant of FIG. 2a together with a coronal abutment part for supporting a cement-retained final restoration.

FIG. 4b is a cross-sectional side view of the arrangement in FIG. 4a.

FIG. 4c is a perspective view of the arrangement in FIG. 4a.

FIG. 4d is a cross-sectional perspective view of the arrangement in FIG. 4a.

FIG. 5b is a cross-sectional side view of the arrangement in FIG. 5a.

FIG. 5c is a cross-sectional perspective view of the arrangement in FIG. 5a.

FIG. 6 is a flow chart of methods according to the present invention.

DETAILED DESCRIPTION

Figure 1A:
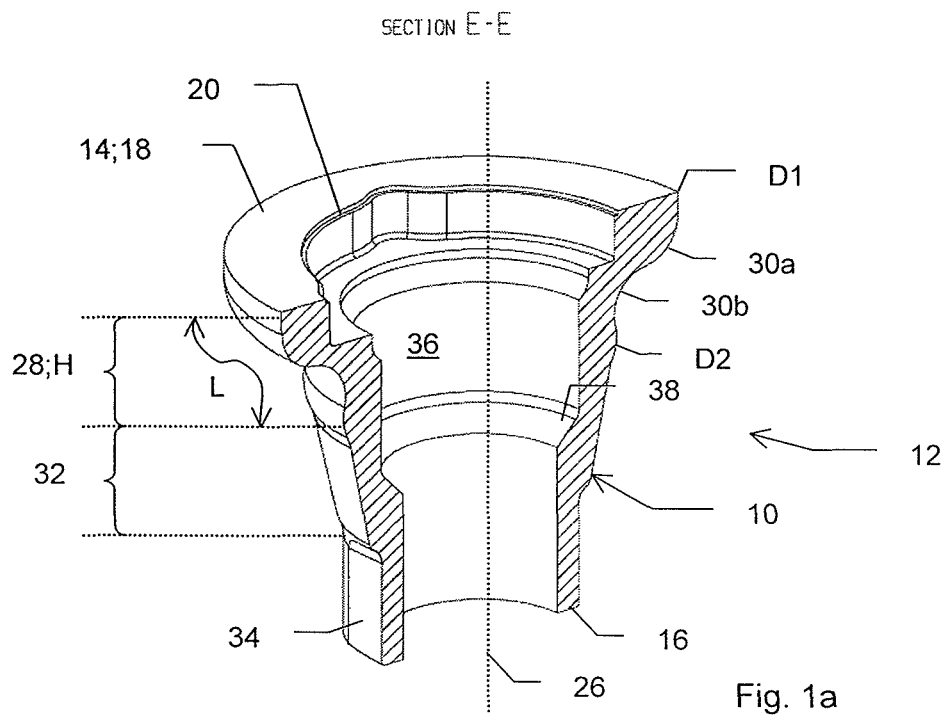
FIG. 1a is a cross-sectional side view of a soft tissue level abutment part of an abutment system according to the present invention.
Figure 1B:
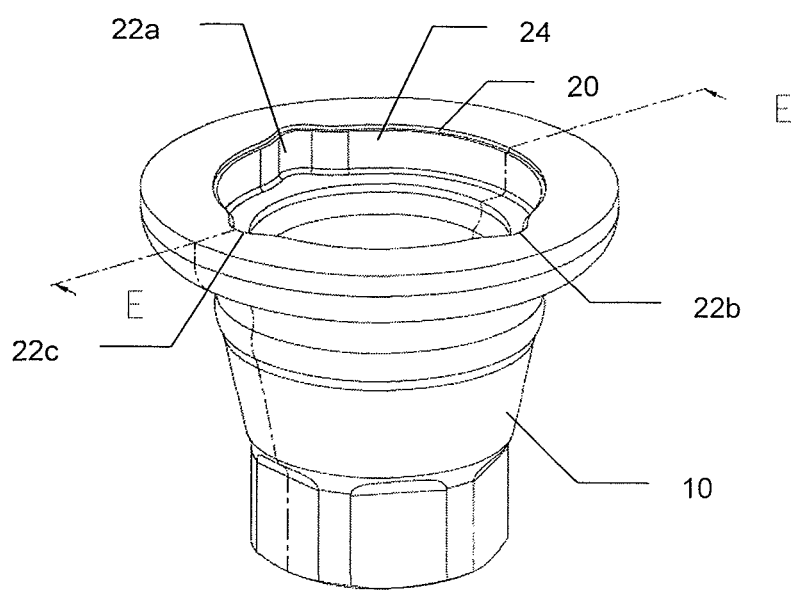

FIGS. 1a-b show a (universal) soft tissue level abutment part 10 of an abutment system 12. The soft tissue level abutment part 10 is 'universal' in that it can be used with both a cement-retained final restoration and a screw-retained prosthetic component, as will be explained further below.

The soft tissue level abutment part 10 is preferably made in one piece, and it can be made of for example titanium or ceramic material (e.g. zirconia).

The soft tissue level abutment part 10 has a coronal end 14 and an apical end 16. At the coronal end 14, the soft tissue level abutment part 10 may have a flat circumferential top surface 18 at the outer perimeter of the soft tissue level abutment part 10. The flat circumferential top surface 18 allows for an effective seal without any cement or the like against another component having a corresponding flat surface.

The flat circumferential top surface 18 has an inner perimeter 20 which may be circular. The inner circular perimeter 20 may accommodate at least one indexing element, here in the form of three concave lobes 22a-c uniformly distributed about the inner circular perimeter 20. The three concave lobes 22a-c extends apically from the inner circular perimeter 20, in an inner side wall 24 of the soft tissue level abutment part 10. The indexing elements may prevent rotation (around the longitudinal axis 26 of the soft tissue level abutment part 10) of a component having corresponding indexing elements being attached to the soft tissue level abutment part 10. Such a component may for instance be a screw-retained single restoration (crown). However, a component without corresponding indexing elements may not be prevented to rotate. Such a component may (only) have a circular interface corresponding to the inner circular perimeter 20. It is appreciated that other indexing elements are possible, for example convex lobes (not shown) instead of the concave lobes 22a-c. Also, the number of indexing elements may be varied.

Extending apically from the flat circumferential top surface 18, the soft tissue level abutment part 10 further has an outer surface 28 devised for exposure to soft tissue or gum. Hence the term 'soft tissue level' abutment part 10.

The outer surface 28 may have a length L that is greater than its height H, in order to increase the soft tissue contact length and improve soft tissue health. The length may for example be about 2.5 mm, while the height may be about 2 mm. The limited height or low profile of the soft tissue level abutment part 10 also enables healing without unnecessary loading of the dental implant (see below).

The outer surface 28 may for instance be at least partly curved between its coronal and apical ends. In the embodiment shown in FIGS. 1a-b, the curved outer surface 28 extends from a larger coronal diameter D1 to a smaller coronal diameter D2, first in a convex shape 30a and then in a concave shape 30b. It is appreciated that other configurations are possible. For example, the outer surface 28 can comprise straight portions that are inclined in relation to each other.

Also, the outer surface 28 may be provided with one or several circumferential or ring-shaped grooves (not shown), whereby sufficient length and additional geometrical locking of the soft tissue may be established.

Also, a lower (apical) portion of the outer surface 28 may be roughened for improved stabilization.

The outer surface 28 transitions apically into an external surface 32 of the soft tissue level abutment part 10. The external surface 32 is generally adapted to abut against an internal connection surface of a bone level dental implant, as will be explained further below. The external surface 32 may be straight but inclined with respect to the longitudinal axis 26 of the soft tissue level abutment part 10, with a decreasing diameter towards the apical end 14 of the soft tissue level abutment part 10. In other words, a conical portion is formed on the soft tissue level abutment part 10. In an alternative embodiment (not shown), the external surface may be parallel to the longitudinal axis 26 of the soft tissue level abutment part 10, depending on what implant the soft tissue level abutment part 10 should be attached to.

At the apical end 14, the soft tissue level abutment part 10 may comprise an interlock portion 34. The interlock portion 34 may comprise an external, generally hexagonal shape that is sized to fit within an interlock recess of the bone level dental implant.

The soft tissue level abutment part 10 further comprises an internal bore 36 extending from the coronal end 14 to the apical end 16 and coinciding with the longitudinal axis 26 of the soft tissue level abutment part 10. In the internal bore 36, there is a seat 38.

Figure 2A:
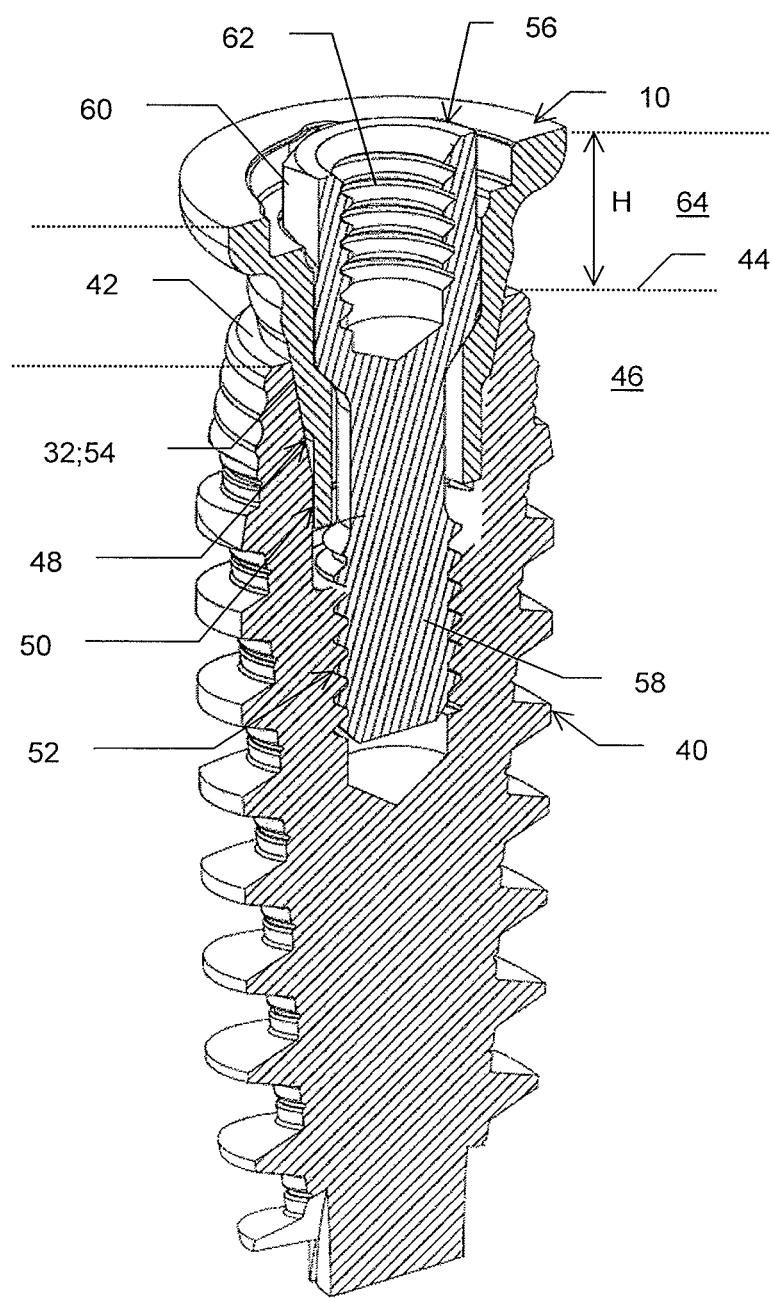
FIG. 2a is a cross-sectional side view of the soft tissue level abutment part of FIG. 1a attached to a dental implant.
Figure 2B:
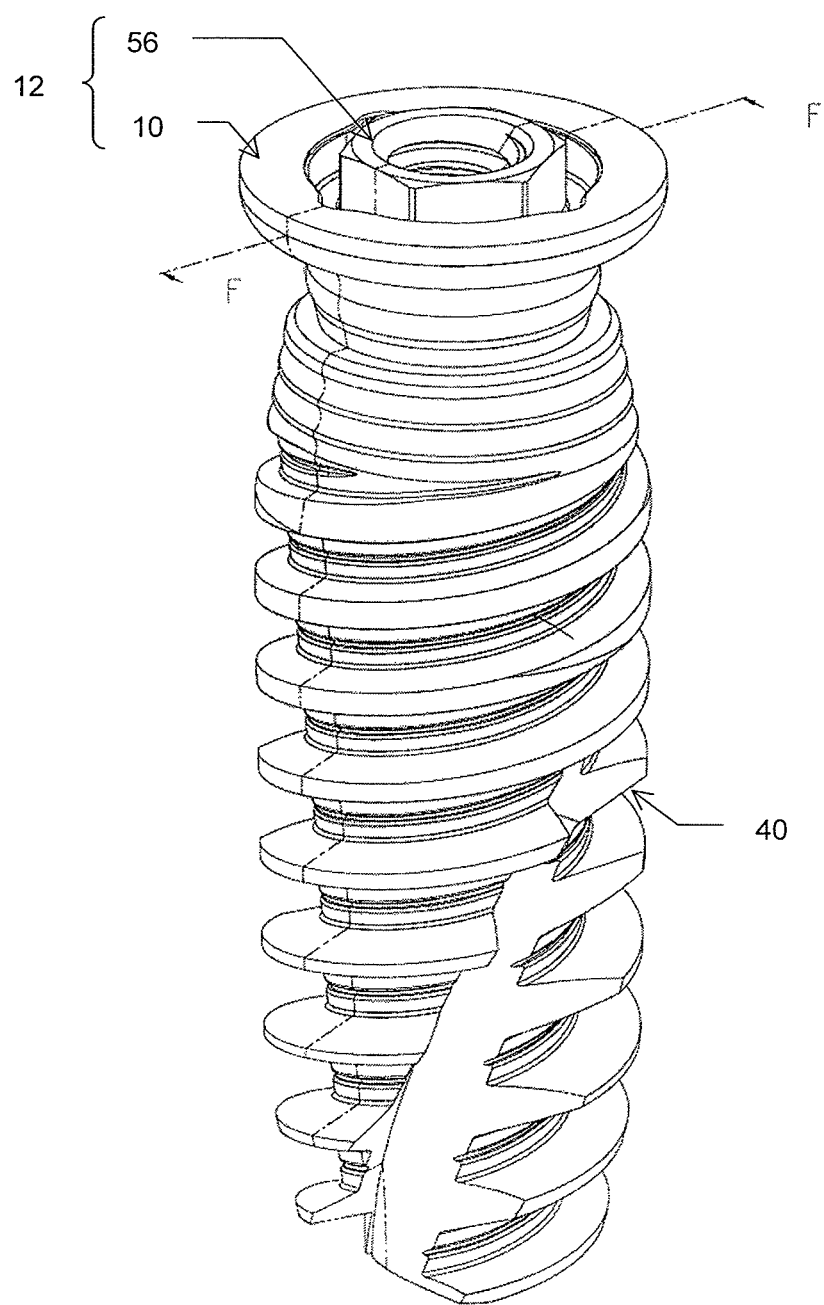

FIGS. 2a-b show the soft tissue level abutment part 10 attached to a dental implant 40. The dental implant 40 is a 'bone level' dental implant, meaning that its coronal end 42 is substantially in level with the edge or crest 44 of the jawbone 46 of a patient, when the dental implant 40 is installed in the jawbone 46.

The dental implant 40 may for example be of the type disclosed in WO 2008/128757 A2, the contents of which herein is incorporated by reference. However, other (bone level) implants may be used as well.

Among other things, the dental implant 40 comprises an internal connection interface that is open to the coronal (or proximal) end 42 of the dental implant 40. The internal connection interface comprises a conical chamber 48, a hexagonal interlock recess 50, and an internally threaded portion 52. The conical chamber 48 has an inclined internal connection surface 54 matching the external surface 32 of the tissue level abutment part 10.

In use, the soft tissue level abutment part 10 is attached to the bone level dental implant 40 by means of an abutment screw 56, as shown in FIGS. 2a-b. The abutment screw 56 may be comprised in the abutment system 12. The abutment screw 56 has an apical external threaded portion 58 for engaging the internally threaded portion 52 of the dental implant 40. Further, the abutment screw 56 has a head 60 that rests against the seat 38 of the soft tissue level abutment part 10. The head 60 may have a coronal internally threaded portion 62. Upon tightening the abutment screw 56, the soft tissue level abutment part 10 is firmly attached to the dental implant 40, and the matching surfaces 32 and 54 create an effective and tight seal.

As also seen in FIG. 2a, the height H of the outer surface 28 of the soft tissue level abutment part 10 may correspond to the height of soft tissue 64 adjacent the installed bone level dental implant 38.

The present abutment system 12 selectively supports both a cement-retained final restoration 66 (see FIGS. 4a-d and 6) and a screw-retained final restoration 68 (see FIGS. 5a-c and 6). In other words, either of a cement-retained final restoration and a screw-retained final restoration can be supported using the same soft tissue level abutment part 10. Also, the abutment system 12 can support other screw-retained prosthetic components, such as a cover screw 70 (see FIG. 3), an impression coping, a bar, etc.

The present invention could also be regarded as a two-piece soft tissue level dental implant, wherein the two pieces are the (bone level) dental implant 40 and the (soft tissue level) abutment part 10.

Figure 3:
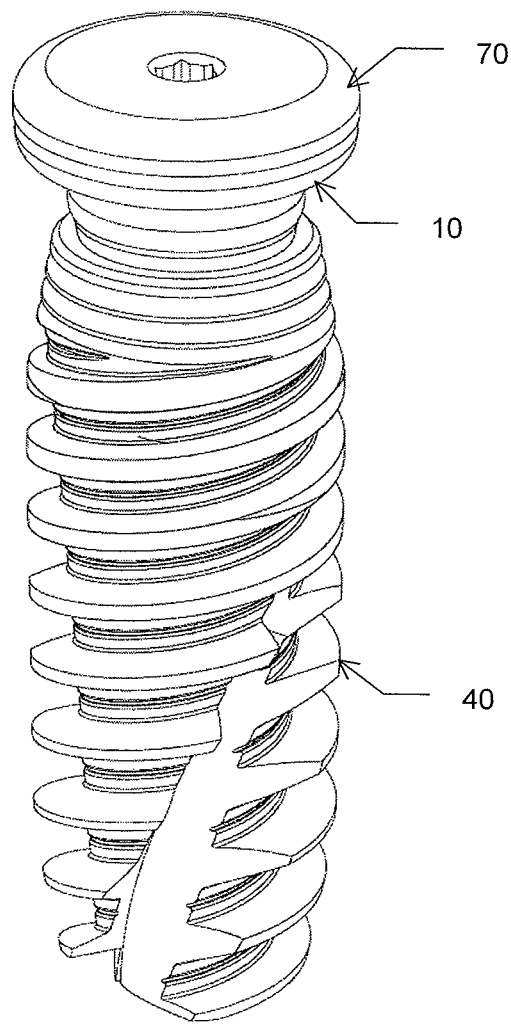
FIG. 3 is a perspective view of the soft tissue level abutment part and dental implant of FIG. 2a together with a cover screw.

In FIG. 3, a cover screw 70 is attached to the a soft tissue level abutment part 10. The cover screw 70 may have an externally threaded portion (not shown) for engagement with the internally threaded portion 62 of the abutment screw 56. The cover screw 70 may further have flat circumferential surface matching the flat circumferential top surface 18 of the soft tissue level abutment part 10, for creating an effective seal between the cover screw 70 and the soft tissue level abutment part 10. The top of the cover screw 70 can be slightly rounded not to damage soft tissue.

In FIGS. 4a-d, the abutment system 12 further comprises a coronal abutment part 72. The coronal abutment part 72 is adapted to be attached to the soft tissue level abutment part 10 by means of a further screw 74. The further screw 74 may also be comprised in the abutment system 12.

Figures 4A, 4B:
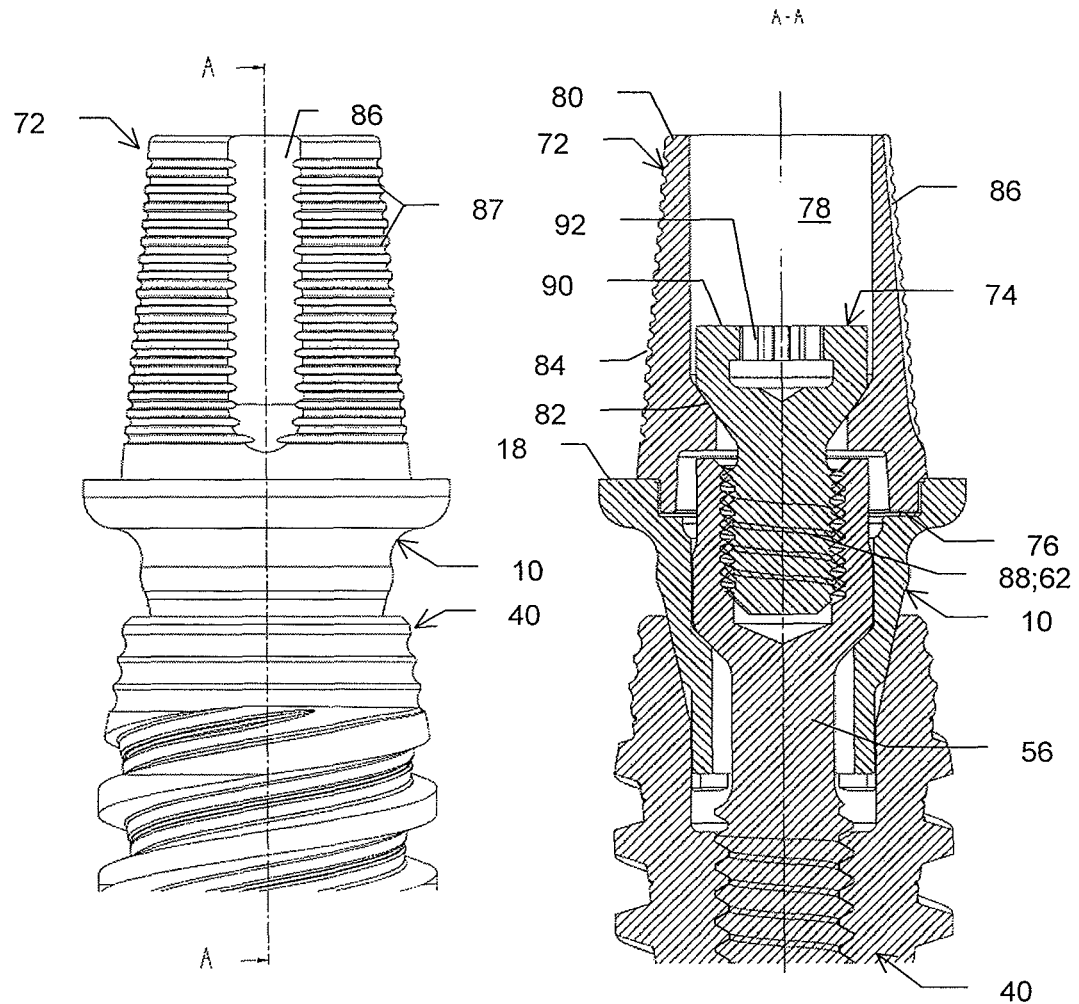
Figures 4C, 4D:
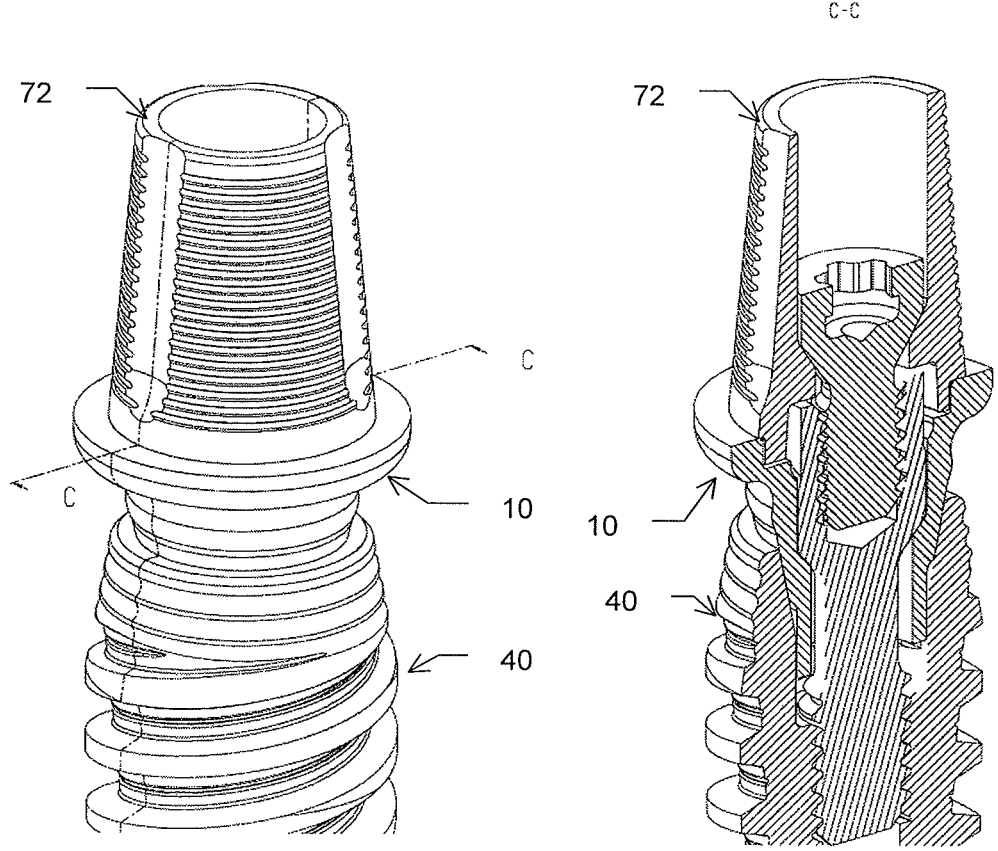

The coronal abutment part 72 has an apical end 76 at least partly matching the coronal end 14 of the soft tissue level abutment part 10, as seen in FIGS. 4b and 4d, such that an effective seal between the abutment parts 10 and 72 can be achieved. The coronal abutment part 72 further comprises an internal bore 78 extending between its coronal end 80 and the apical end 76. In the internal bore 78, there is a seat 82. The coronal abutment part 72 is further adapted to support a cement-retained final restoration (not shown in FIGS. 4a-d), such as a crown or bridge. To this end, an outer surface 84 of the coronal abutment part 72 may include one or several longitudinal grooves 86 for accommodating cement. The outer surface 84 may also comprise a plurality of (smaller) transversal grooves and ridges 87. Further, the coronal abutment part may be designed such that a portion of the flat circumferential top surface 18 remains exposed when the coronal abutment part 72 is attached to the soft tissue level abutment part 10. The exposed portion of the flat circumferential top surface 18 may also serve as a support for the cement-retained final restoration.

In use, the coronal abutment part 72 is attached to the soft tissue level abutment part 10 by means of the further screw 74. The further screw 74 has an apical external threaded portion 88 for engaging the internally threaded portion 62 of the abutment screw 56. Also, the further screw 74 has a head 90 that rests against the seat 82 of the coronal abutment part 72. The head 90 may have a coronal tool socket 92. Upon tightening the further screw 74, the coronal abutment part 72 is firmly attached to the soft tissue level abutment part 10. Thereafter, the cement-retained final restoration may be cemented on top of the coronal abutment part 72 in a manner known per se.

Figure 5B:
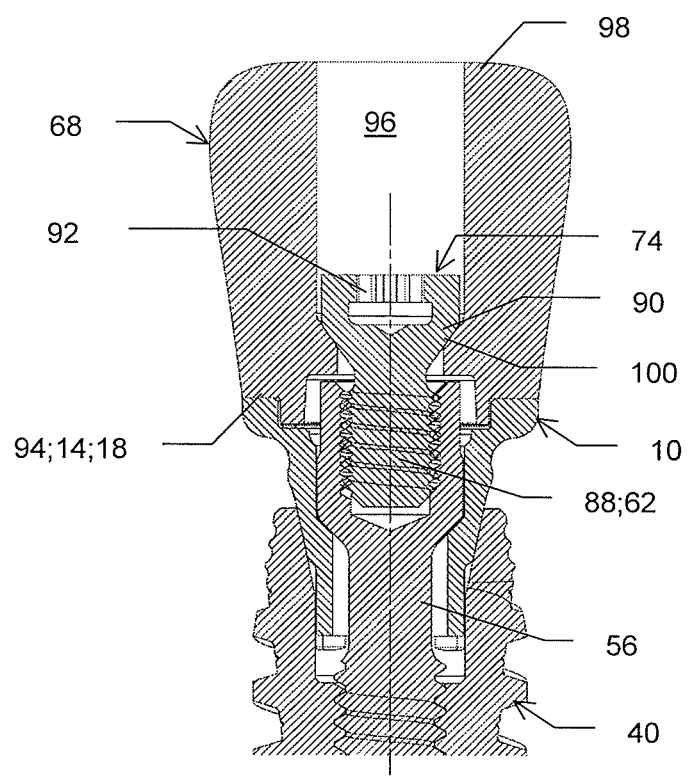
Figure 5A:
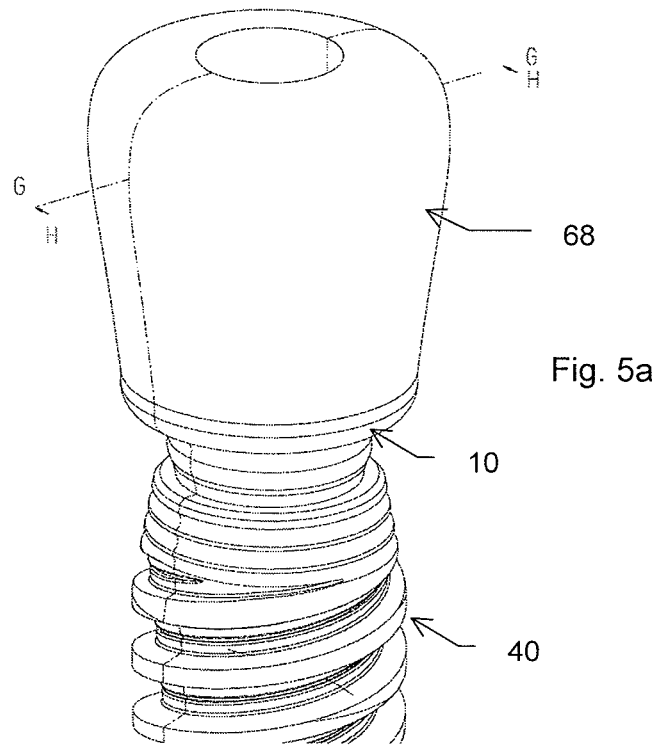
FIG. 5a is a perspective view of the soft tissue level abutment part and dental implant of FIG. 2a together with a screw-retained final restoration.
Figure 5C:
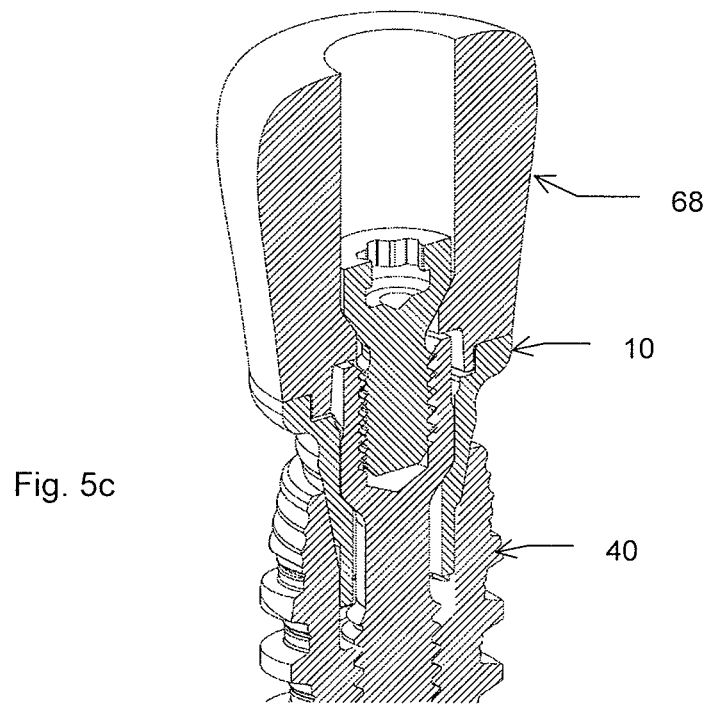

FIGS. 5a-c show a screw-retained final restoration 68 attached to the soft tissue level abutment part 10 by means of a further screw 74. The screw-retained final restoration 68 in FIGS. 5a-c is embodied as a crown, but it can also be a bridge, etc.

The screw-retained final restoration 68 has an apical end 94 at least partly matching the coronal end 14 of the soft tissue level abutment part 10, as seen particularly in FIGS. 5b-c, such that an effective seal between the soft tissue level abutment part 10 and the screw-retained final restoration 68 can be achieved. The screw-retained final restoration 68 may be designed such that no portion of the flat circumferential top surface 18 remains exposed when the screw-retained final restoration 68 is attached to the soft tissue level abutment part 10. This ensures a smooth transition between the screw-retained final restoration 68 and the soft tissue level abutment part 10. The screw-retained final restoration 68 further comprises an internal bore 96 extending between its coronal end 98 and the apical end 94. In the internal bore 96, there is a seat 100.

In use, the screw-retained final restoration 68 is directly attached to the soft tissue level abutment part 10 by means of the further screw 74. The further screw 74 has an apical external threaded portion 88 for engaging the internally threaded portion 62 of the abutment screw 56. Also, the further screw 74 has a head 90 that rests against the seat 100 of the screw-retained final restoration 68. The head 90 may have a coronal tool socket 92. Upon tightening the further screw 74, the screw-retained final restoration 68 is firmly attached to the soft tissue level abutment part 10. Thereafter, the open portion of the internal bore 96 may be filled with a filler (not shown).

With reference to FIG. 6, the abutment system 12 may be used in the following way:

First, the bone level dental implant 40 is installed (a) by a surgeon in the jawbone 46 of a patient in a manner known per se. The dental implant 40 should be installed such that the coronal end 42 of the dental implant 40 is substantially in level with the upper edge 44 of the jawbone 46.

Then, after installation, the soft tissue level abutment part 10 is attached (b) to the dental implant 40 by the surgeon by means of the abutment screw 56. This soft tissue level abutment part 10 will normally not be removed after it has been attached to the implant 40. The outer surface 28 is here exposed to soft tissue 64. The soft tissue level abutment part 10 may be attached to the dental implant 40 immediately after the dental implant 40 has been installed.

A prosthodontist, which typically is not the same person as the surgeon, is thereafter free to decide or select (c) which one of a cement-retained final restoration 66 and a screw-retained final restoration 68 that should be used. This makes the present system very flexible.

The selected final restoration may then be attached (d) as described in relation to FIGS. 4a-d or FIGS. 5a-c, i.e. without having to remove the soft tissue level abutment part 10, and without breaking any soft tissue seal. Also, any intermediate operations, such as attaching the cover screw or an impression coping to the soft tissue level abutment part 10 can be carried out without breaking any soft tissue seal. Step (d) may be performed several weeks or months after step (b) (attachment of soft tissue level abutment part 10), to allow for osseointegration of the dental implant 40. Alternatively, an immediate/early loading protocol can be used.

Further, several soft tissue level abutment parts 10 with different diameters (widths) and/or different heights may be provided, to cater for various clinical situations. This makes the present system and method more flexible than a one-piece soft tissue level dental implant system.

The person skilled in the art realizes that the present invention by no means is limited to the preferred embodiments described above. On the contrary, many modifications and variations are possible within the scope of the appended claims.

What is claimed is:

1. A dental method, which comprises:
   providing an abutment system including a universal soft tissue level abutment part adapted to be attached to a bone level dental implant;
   attaching the universal soft tissue level abutment part to an internal connection interface of the bone level dental implant installed in the jawbone of a patient with an abutment screw such that an apical portion of the universal soft tissue level abutment part adjacent and above the coronal end of the bone level dental implant has an outer diameter smaller than an outer diameter of the bone level dental implant at the coronal end and a coronal portion of the universal soft tissue level abutment part has an outer diameter larger than the outer diameter of the apical portion of the universal soft tissue level abutment part above the coronal end of the bone level dental implant, the universal soft tissue level abutment part comprising a soft tissue collar having a coronal flat circumferential platform, the coronal flat circumferential platform having an inner perimeter accommodating at least one indexing element configured to prevent rotation of a component attached to the coronal portion of the universal soft tissue level abutment part, wherein the abutment screw has an apical externally threaded portion configured to engage the bone level dental implant and a coronal internally threaded portion;
   coupling a temporary screw retained component to the universal soft tissue level abutment part with a further screw, wherein the further screw has an apical externally threaded portion configured to engage with the coronal internally threaded portion of the abutment screw such that the apical externally threaded portion of the further screw sits at least partially within the soft tissue level abutment part;
   with the temporary screw retained component coupled to the universal soft tissue level abutment part, leaving the universal soft tissue level abutment part attached to the bone level dental implant during a first period;
   wherein the abutment system is adapted to selectively support both a cement-retained final restoration and a screw-retained final restoration; and
   after the first period, removing the temporary screw-retained component and attaching the selected final restoration to the universal soft tissue level abutment part without removing the universal soft tissue level abutment part from the bone level dental implant,
   wherein the final restoration comprises a coronal abutment part having a corresponding at least one indexing element at an apical end of the coronal abutment part, the corresponding at least one indexing element configured to attach to the at least one indexing element accommodated by the inner perimeter of the coronal flat circumferential platform at a coronal end of the universal soft tissue level abutment part thereby preventing rotation of the final restoration, and
   wherein the corresponding at least one indexing element of the coronal abutment part does not engage with an anti-rotational feature of a crown supported on the coronal abutment part.

2. The method of claim 1, wherein the universal soft tissue level abutment part remains attached to the bone level dental implant during subsequent steps of the method, which include:
   selecting one of a cement-retained final restoration and a screw-retained final restoration; and
   attaching the selected final restoration to the abutment system.

3. The method of claim 2, wherein in case the selected final restoration is the cement-retained final restoration, attaching the selected final restoration to the abutment system includes attaching the cement-retained final restoration to the coronal abutment part attached to the universal soft tissue level abutment part, and wherein in case the selected final restoration is the screw-retained final restoration, attaching the selected final restoration to the abutment system includes attaching the screw-retained final restoration directly to the universal soft tissue level abutment part.

4. The method according to claim 1, wherein the universal soft tissue level abutment part is attached to the bone level dental implant immediately after the bone level dental implant is installed in the jawbone of the patient.

5. The method according to claim 2, wherein the bone level dental implant is allowed to at least partly osseointegrate before the selected final restoration is attached.

6. The method according to claim 1, wherein the bone level dental implant is installed in the jawbone such that the coronal end of the bone level dental implant is substantially in level with the edge of the jawbone.

7. The method according to claim 1, wherein the attached universal soft tissue level abutment part has an outer surface exposed to soft tissue.

8. The method according to claim 1, comprising coupling a second temporary screw retained component after removing the first temporary screw retained component and before attaching the selected final restoration.

9. The method according to claim 1, wherein the component attached to the universal soft tissue level abutment part comprises the selected final restoration.

10. The method according to claim 1, wherein the at least one indexing element is exposed to the coronal end of the universal soft tissue level abutment part.

11. The method according to claim 1, wherein the at least one indexing element comprises one or more lobes.

12. The method according to claim 11, wherein the one or more lobes extend apically from the inner perimeter.

13. The method according to claim 11, wherein the at least one indexing element comprises one or more concave lobes.

14. The method according to claim 11, wherein the at least one indexing element comprises one or more convex lobes.

15. The method according to claim 11, wherein the at least one indexing element comprises three lobes.

16. A dental method, which comprises:
providing an abutment system including a universal soft tissue level abutment part adapted to be attached to a bone level dental implant;
attaching an interlock portion at an apical end of the universal soft tissue level abutment part to an internal connection interface of the bone level dental implant installed in the jawbone of a patient with an abutment screw such that an apical portion of the universal soft tissue level abutment part adjacent and above the coronal end of the bone level dental implant has an outer diameter smaller than an outer diameter of the bone level dental implant at the coronal end and a coronal portion of the universal soft tissue level abutment part has an outer diameter larger than the outer diameter of the apical portion of the universal soft tissue level abutment part above the coronal end of the bone level dental implant, the universal soft tissue level abutment part comprising a soft tissue collar having a coronal flat circumferential platform, the coronal flat circumferential platform having an inner perimeter accommodating at least one indexing element configured to prevent rotation of a component attached to the coronal portion of the universal soft tissue level abutment part, wherein the abutment screw has an apical externally threaded portion configured to engage the bone level dental implant and a coronal internally threaded portion;
coupling a temporary screw retained component to the universal soft tissue level abutment part with a further screw, wherein the further screw has an apical externally threaded portion configured to engage with the coronal internally threaded portion of the abutment screw such that the apical externally threaded portion of the further screw sits at least partially within the soft tissue level abutment part;
with the temporary screw retained component coupled to the universal soft tissue level abutment part, leaving the universal soft tissue level abutment part attached to the bone level dental implant during a first period;
wherein the abutment system is adapted to selectively support both a cement-retained final restoration and a screw-retained final restoration; and
after the first period, removing the temporary screw-retained component and attaching the selected final restoration to the universal soft tissue level abutment part without removing the universal soft tissue level abutment part from the bone level dental implant,
wherein the final restoration comprises a coronal abutment part having a corresponding at least one indexing element at an apical end of the coronal abutment part, the corresponding at least one indexing element configured to cover and attach to the at least one indexing element accommodated by the inner perimeter of the coronal flat circumferential platform at a coronal end of the universal soft tissue level abutment part thereby preventing rotation of the final restoration, the coronal abutment part configured to support a crown thereon.

17. The method according to claim 16, wherein the bone level dental implant is allowed to at least partly osseointegrate before the final restoration is attached.

18. The method according to claim 16, wherein the at least one indexing element comprises one or more lobes.

* * * * *